(12) United States Patent
Stoessel et al.

(10) Patent No.: US 9,139,765 B2
(45) Date of Patent: Sep. 22, 2015

(54) ORGANIC ELECTROLUMINESCENT DEVICE

(75) Inventors: Philipp Stoessel, Frankfurt am Main (DE); Esther Breuning, Ober-Ramstadt (DE); Dominik Joosten, Frankfurt am Main (DE)

(73) Assignee: Merck Patent GmbH (DE)

( * ) Notice: Subject to any disclaimer, the term of this patent is extended or adjusted under 35 U.S.C. 154(b) by 23 days.

(21) Appl. No.: 13/643,615

(22) PCT Filed: Mar. 24, 2011

(86) PCT No.: PCT/EP2011/001494
§ 371 (c)(1),
(2), (4) Date: Oct. 26, 2012

(87) PCT Pub. No.: WO2011/134577
PCT Pub. Date: Nov. 3, 2011

(65) Prior Publication Data
US 2013/0046094 A1    Feb. 21, 2013

(30) Foreign Application Priority Data
Apr. 27, 2010   (DE) .................. 10 2010 018 321

(51) Int. Cl.
| | | |
|---|---|---|
| *C07F 9/6584* | (2006.01) | |
| *C09K 11/06* | (2006.01) | |
| *H05B 33/14* | (2006.01) | |
| *H01L 51/52* | (2006.01) | |
| *H01L 51/54* | (2006.01) | |
| *C07F 9/46* | (2006.01) | |
| *C07F 9/6568* | (2006.01) | |
| *C07F 9/6587* | (2006.01) | |
| *C09B 55/00* | (2006.01) | |
| *C09B 57/00* | (2006.01) | |
| *H01L 51/50* | (2006.01) | |

(52) U.S. Cl.
CPC . *C09K 11/06* (2013.01); *C07F 9/46* (2013.01); *C07F 9/6584* (2013.01); *C07F 9/6587* (2013.01); *C07F 9/65686* (2013.01); *C09B 55/006* (2013.01); *C09B 55/009* (2013.01); *C09B 57/00* (2013.01); *H05B 33/14* (2013.01); *C09K 2211/1096* (2013.01); *C09K 2211/185* (2013.01); *H01L 51/5016* (2013.01); *H01L 51/5052* (2013.01); *H01L 51/5096* (2013.01)

(58) Field of Classification Search
CPC ... C07F 9/6584; C09K 11/06; H01L 51/0032; H01L 51/5064; H01L 51/5032; H05B 33/14
USPC ............................................. 568/12; 428/917
See application file for complete search history.

(56) References Cited

U.S. PATENT DOCUMENTS

| | | |
|---|---|---|
| 2006/0208221 A1 | 9/2006 | Gerhard et al. |
| 2006/0255332 A1 | 11/2006 | Becker et al. |
| 2011/0140043 A1 | 6/2011 | Stoessel et al. |

FOREIGN PATENT DOCUMENTS

| | | |
|---|---|---|
| DE | 102008033943 A1 | 1/2010 |
| WO | WO-2005003253 A3 | 4/2005 |
| WO | WO-2004093207 A3 | 6/2005 |

OTHER PUBLICATIONS

Hulikal V., www.hwb.gov.in/htmldocs/nahwd2010/L15.pdf. Abstract p. 1, 2010.*
International Search Report for PCT/EP2011/001494 mailed Jul. 28, 2011.
Romanenko, E.A., et al., "The Investigation of the Intramolecular Transmission Effects in Cyclic Diazaphosphorines", Journal of Molecular Structure, vol. 83, (1982), pp. 337-340.
Döpp, H., et al., XP009149759, Science of Synthesis, (2004), pp. 223-355.
Trupti, N.D., et al., XP002649740, Agnew. Chem., vol. 96, No. 12, (1984), pp. 984-985.
Schaefer, Werner, et al., "Nature of Bonding in λ5-Phosphorins1", XP002649741, Journal of the American Chemical Society, vol. 98, No. 15, (1976), pp. 4410-4418.
Kanter, Hartmut, et al., XP002649742, "1,1-Dihalogen-λ5-Phosphorine", Chem. Ber., vol. 110, (1977), pp. 395-422.
Schmidbaur, Hubert, et al., "Syntheses and Molecular Structures of an Isoelectronic Series of (2-Hetero-)1,3-Diphosphabenzenes", XP002649743, Chem. Ber., vol. 124, (1991), pp. 1525-1530.

* cited by examiner

*Primary Examiner* — Venkataraman Balasubramanian
(74) *Attorney, Agent, or Firm* — Drinker Biddle & Reath LLP

(57) ABSTRACT

The present invention relates to electronic devices, in particular organic electroluminescent devices, which comprise compounds of the formula (1) or (2), and to the corresponding compounds and to the use thereof in organic electroluminescent devices.

6 Claims, No Drawings

ORGANIC ELECTROLUMINESCENT DEVICE

RELATED APPLICATIONS

This application is a national stage application (under 35 U.S.C. §371) of PCT/EP2011/001494, filed Mar. 24, 2011, which claims benefit of German Application No. 10 2010 018 321.0, filed Apr. 27, 2010.

The present invention relates to organic electroluminescent devices and to materials for use in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). For quantum-mechanical reasons, an up to four-fold energy and power efficiency is possible using organometallic compounds as phosphorescent emitters. In general, there is still a need for improvement, in particular with respect to efficiency, operating voltage and lifetime, both in the case of OLEDs which exhibit singlet emission and also in the case of OLEDs which exhibit triplet emission. This applies, in particular, to OLEDs which emit in the relatively short-wave region, i.e. green and in particular blue.

The properties of OLEDs are not determined only by the emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties.

In accordance with the prior art, ketones (for example in accordance with WO 2004/093207 or WO 2010/006680) or phosphine oxides (for example in accordance with WO 2005/003253), inter alia, are used as matrix materials for phosphorescent emitters. However, there is still a need for improvement, in particular with respect to the efficiency and lifetime of the device, on use of these matrix materials, as in the case of other matrix materials.

The object of the present invention is the provision of compounds which are suitable for use in a fluorescent or phosphorescent OLED, for example as matrix material or as hole-transport/electron-blocking material or exciton-blocking material or as electron-transport or hole-blocking material, and which result in good device properties on use in an OLED, and the provision of the corresponding electronic device.

Surprisingly, it has been found that certain compounds described in greater detail below achieve this object and result in good properties of the organic electroluminescent device, in particular with respect to the lifetime, efficiency and operating voltage. The present invention therefore relates to electronic devices, in particular organic electroluminescent devices, which comprise compounds of this type, and to the corresponding preferred compounds.

The present invention relates to an electronic device comprising at least one compound of the following formula (1) or (2),

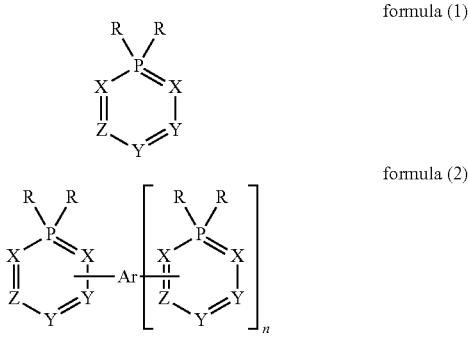

where the following applies to the symbols and indices used:

X, Y is on each occurrence, identically or differently, $CR^1$, N, P or $PR_2$;

Z is on each occurrence, identically or differently, $CR^1$ or N;

Ar is on each occurrence, identically or differently, an aromatic or heteroaromatic ring system having 5 to 60 aromatic ring atoms, which may be substituted by one or more radicals $R^1$;

R is on each occurrence, identically or differently, $N(R^2)_2$, $N(Ar^1)_2$, $C(=O)R^2$, $C(=O)Ar^1$, $P(=O)(Ar^1)_2$, $S(=O)Ar^1$, $S(=O)_2Ar^1$, $CR^2=CR^2Ar^1$, CN, $Si(R^2)_3$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems; two or more substituents R together with the atoms to which they are bonded may also form a mono- or polycyclic aliphatic or aromatic ring system with one another here;

$R^1$ is on each occurrence, identically or differently, H, D, F, Cl, Br, I, $N(R^2)_2$, $N(Ar^1)_2$, $C(=O)R^2$, $C(=O)Ar^1$, $P(=O)(Ar^1)_2$, $S(=O)Ar^1$, $S(=O)_2Ar^1$, $CR^2=CR^2Ar^1$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems;

Ar¹ is on each occurrence, identically or differently, an aromatic or heteroaromatic ring system having 5 to 30 aromatic ring atoms, which may be substituted by one or more radicals R²;

R² is selected from the group consisting of H, D, F, CN, aliphatic hydrocarbon radical having 1 to 20 C atoms, aromatic or heteroaromatic ring system having 5 to 30 aromatic ring atoms, in which one or more H atoms may be replaced by D, F, Cl, Br, I or CN, where two or more adjacent substituents R² may form a mono- or polycyclic, aliphatic, aromatic or heteroaromatic ring system with one another;

n is 1 to 10, preferably 1, 2, 3, 4, 5 or 6.

The bonding of Ar to the corresponding phosphorus-containing ring takes place here either via a group X or Y, where in this case X or Y stands for C or PR and the group Ar is bonded to this C or PR, or via a group Z, where in this case Z stands for C, or via the phosphorus explicitly depicted in the formula, where in this case, instead of two radicals R, only one radical R is bonded to the phosphorus.

Furthermore, an index n which is greater than 1 means that a corresponding number of phosphorus-containing rings is bonded to the group Ar.

An aryl group in the sense of this invention contains 6 to 40 C atoms; a heteroaryl group in the sense of this invention contains 1 to 39 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 1 to 59 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be linked by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a short alkyl group. Furthermore, systems in which a plurality of aryl and/or heteroaryl groups are linked to one another by a single bond, such as, for example, biphenyl, terphenyl or bipyridine, are intended to be taken to be an aromatic or heteroaromatic ring system.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoro-ethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, $SO$, $SO_2$, $NR^1$, O, S or $CONR^1$; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms, which may also in each case be substituted by the above-mentioned radicals R¹ or a hydrocarbon radical and which may be linked to the aromatic or heteroaromatic ring system via any desired positions, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6, 7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, each of the phosphorus-containing rings contains a maximum of three phosphorus atoms. Thus, in total a maximum of two symbols X or Y preferably stand for P or $PR_2$.

In a further preferred embodiment of the invention, X and Y stand, identically or differently on each occurrence, for $CR^1$, N or $PR_2$.

In a further preferred embodiment of the invention, each of the phosphorus-containing rings contains at least one and a maximum of three nitrogen atom. Thus, in total at least one and a maximum of three of the symbols X, Y or Z preferably stand for N.

In a particularly preferred embodiment of the invention, each phosphorus-containing ring in the compound of the formula (1) or formula (2) contains at least one P—N bond. Thus, at least one symbol X particularly preferably stands for N.

In a very particularly preferred embodiment of the invention, each phosphorus-containing ring in the compound of the formula (1) or formula (2) contains at least one N—P—N unit and/or at least one P—N—P unit. Thus, both symbols X very particularly preferably stand for N and/or one symbol X stands for N and the group Y bonded to this group X stands for P or $PR_2$, in particular for $PR_2$.

Particular preference is therefore given to the compounds of the following formulae (3), (4), (5) and (6), formula (3)
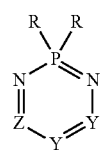

formula (4)
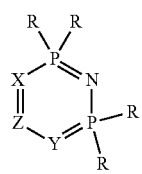

formula (5)
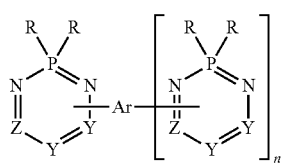

formula (6)
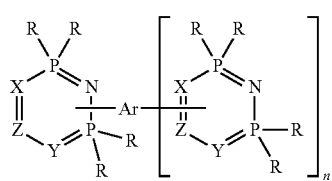

where the symbols and indices used have the meanings mentioned above.

In a preferred embodiment of the compounds of the formula (3) to (6), both groups X stand for N, and the group Z stands for CR. Particular preference is given to the compounds of the following formulae (3a), (4a), (5a) and (6a), formula (3a)
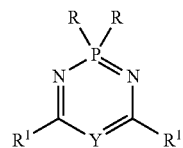

formula (4a)
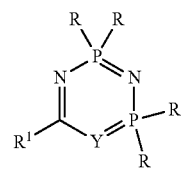

formula (5a)
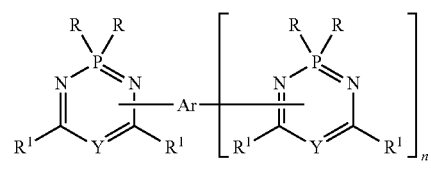

formula (6a)
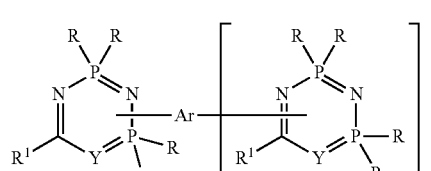

where the symbols and indices used have the meanings mentioned above.

Preferred embodiments of the compounds of the formula (3a) to (6a) are compounds in which the symbol Y stands for N, i.e. the compounds of the following formulae (3b), (4b), (5b) and (6b), formula (3b)
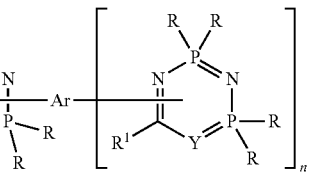

formula (4b)
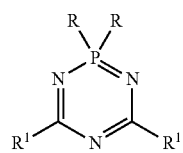

formula (5b)
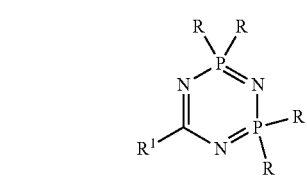

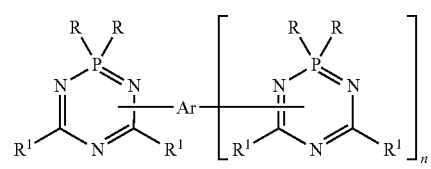

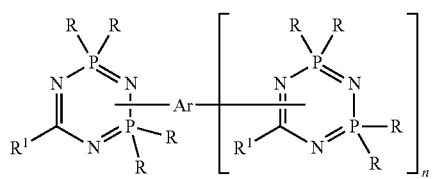
formula (6b)

where the symbols and indices used have the meanings mentioned above.

In a further preferred embodiment of the invention, the group Ar stands for an aromatic or heteroaromatic ring system having 5 to 30 aromatic ring atoms, particularly preferably having 5 to 24 aromatic ring atoms. If the compound of the formula (1) or (2) is used as matrix material for a phosphorescent electroluminescent device, preferably none of the aryl or heteroaryl groups of the aromatic or heteroaromatic ring system contains more than 10 aromatic ring atoms. Preferred groups Ar for use as triplet matrix material are therefore built up from in each case one or more of the groups benzene, pyridine, pyrimidine, pyridazine, pyrazine, triazine, pyrrole, thiophene, furan, naphthalene, quinoline, isoquinoline, quinoxaline, indole, benzothiophene or benzofuran, each of which may be substituted by one or more radicals $R^1$. Particularly preferred groups Ar are built up from in each case one or more groups benzene, pyridine, pyrimidine, pyridazine, pyrazine or triazine, each of which may be substituted by one or more radicals $R^1$, in particular benzene, which may be substituted by one or more radicals $R^1$. Further preferred groups Ar for use as triplet matrix material are triphenylene and carbazole. Likewise suitable are combinations of the aryl and heteroaryl groups mentioned as preferred. If the compound of the formula (1) or (2) is used in another function, for example as electron-transport material, preferred groups Ar may thus also contain larger condensed aryl or heteroaryl groups, for example anthracene, pyrene or perylene, each of which may be substituted by one or more radicals $R^1$.

In a particularly preferred embodiment of the invention, Ar is selected from the group consisting of the units of the following formulae (7) to (18), where the dashed bond in each case indicates the linking to one of the phosphorus-containing rings:

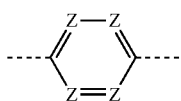
formula (7)

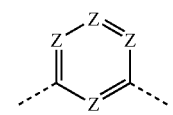
formula (8)

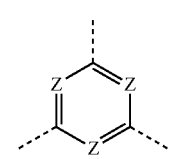
formula (9)

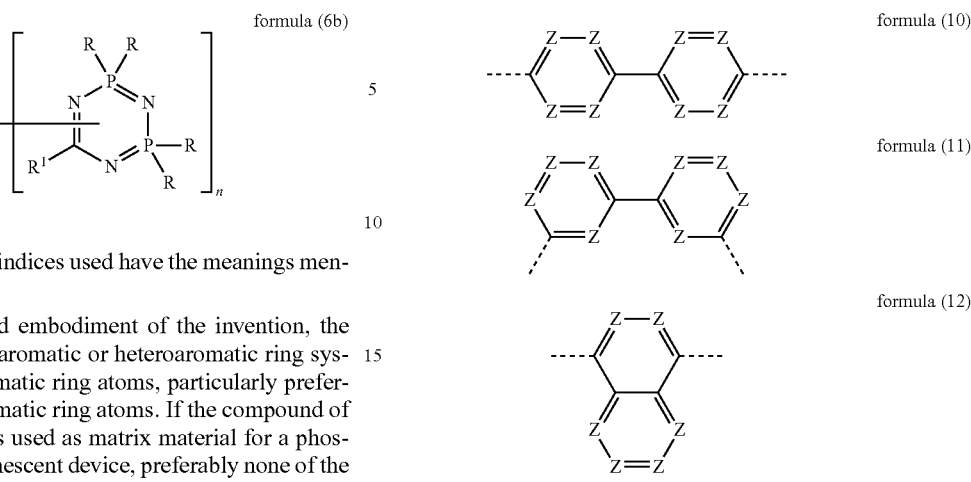
formula (10)

formula (11)

formula (12)

formula (13)

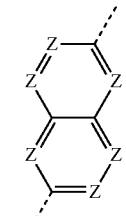

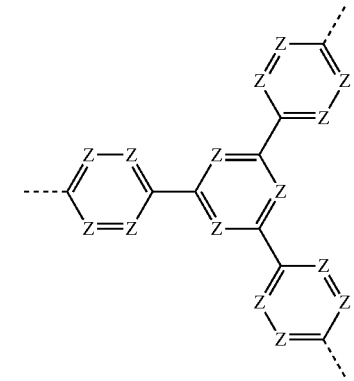
formula (14)

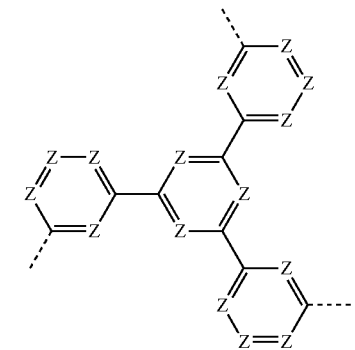
formula (15)

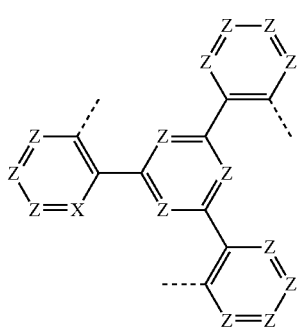

formula (16)

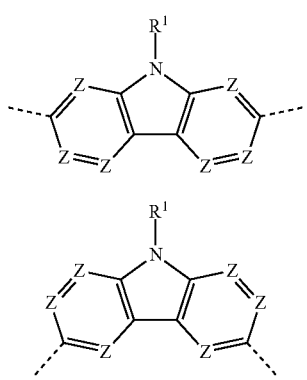

formula (17)

formula (18)

where the symbols used have the meanings mentioned above.

In a further preferred embodiment of the invention, the index n=1, 2, 3 or 4, particularly preferably 1, 2 or 3, very particularly preferably 1 or 2.

In a preferred embodiment of the invention, the radicals R are selected, identically or differently on each occurrence, from the group consisting of $N(R^2)_2$, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by O and where one or more H atoms may be replaced by D or F, or an aromatic or heteroaromatic ring system having 5 to 30 aromatic ring atoms, which may in each case be substituted by one or more radicals $R^2$, or an aryloxy or heteroaryloxy group having 5 to 20 aromatic ring atoms, which may be substituted by one or more radicals $R^2$, or an aralkyl or heteroaralkyl group having 5 to 20 aromatic ring atoms, which may be substituted by one or more radicals $R^2$; two or more substituents R together with the phosphorus atom to which they are bonded may also form a mono- or polycyclic aliphatic or aromatic ring system with one another here.

In a particularly preferred embodiment of the invention, the radicals R which are bonded to the phosphorus are selected, identically or differently on each occurrence, from the group consisting of a straight-chain alkyl or alkoxy group having 1 to 4 C atoms or a branched alkyl or alkoxy group having 3 or 4 C atoms, each of which may be substituted by one or more radicals $R^2$, where one or more H atoms may be replaced by D or F, or an aromatic or heteroaromatic ring system having 5 to 24 aromatic ring atoms, which may in each case be substituted by one or more radicals $R^2$; two or more substituents R together with the phosphorus atom to which they are bonded may also form a mono- or polycyclic aliphatic or aromatic ring system with one another here.

It should again be pointed out that the radicals R which are bonded to the same phosphorus atom may also form a ring system with one another and may thus form a spiro system, as depicted below by way of example for an aromatic and an aliphatic ring system:

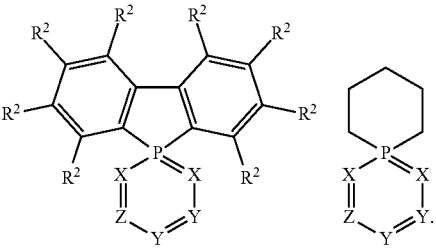

In a further preferred embodiment of the invention, the radical $R^1$ which is bonded to the carbon of the phosphacycle is selected, identically or differently on each occurrence, from the group consisting of H, D, F, $N(Ar^1)_2$, $C(=O)Ar^1$, $P(=O)(Ar^1)_2$, CN, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by O and where one or more H atoms may be replaced by D or F, or an aromatic or heteroaromatic ring system having 5 to 30 aromatic ring atoms, which may in each case be substituted by one or more radicals $R^2$.

In a particularly preferred embodiment of the invention, the radical $R^1$ which is bonded to the carbon of the phosphacycle is selected, identically or differently on each occurrence, from the group consisting of H, D, $C(=O)Ar^1$, a straight-chain alkyl group having 1 to 4 C atoms or a branched alkyl group having 3 or 4 C atoms, each of which may be substituted by one or more radicals $R^2$, where one or more H atoms may be replaced by D or F, or an aromatic or heteroaromatic ring system having 5 to 24 aromatic ring atoms, which may in each case be substituted by one or more radicals $R^2$.

If the compound of the formula (1) or formula (2) is employed as triplet matrix material and the radicals R or $R^1$ stand for an aromatic or heteroaromatic ring system, it is preferred for this to contain no aryl groups having more than two condensed aryl rings. This preference is explained by the frequently low triplet level of aryl groups having more than two condensed aryl rings, meaning that compounds of this type are less suitable as triplet matrix material. The aromatic or heteroaromatic ring system particularly preferably contains no condensed aryl groups. Preferred aromatic or heteroaromatic ring systems R or $R^1$ for use as triplet matrix material are therefore built up from in each case one or more of the groups benzene, pyridine, pyrimidine, pyridazine, pyrazine, triazine, pyrrole, thiophene, furan, naphthalene, quinoline, isoquinoline, quinoxaline, indole, benzothiophene or benzofuran, each of which may be substituted by one or more radicals $R^2$. Particularly preferred groups Ar are built up from in each case one or more groups benzene, pyridine, pyrimidine, pyridazine, pyrazine or triazine, each of which may be substituted by one or more radicals $R^2$, in particular benzene, which may be substituted by one or more radicals $R^2$. Further preferred groups R or $R^1$ for use as triplet matrix material are triphenylene and carbazole. Preference is likewise given to combinations of the aryl and heteroaryl groups mentioned as preferred. If the compound of the formula (1) or (2) is used in another function, for example as electron-transport material, preferred groups R or $R^1$ may thus also contain larger condensed aryl or heteroaryl groups, for example anthracene, pyrene or perylene, each of which may be substituted by one or more radicals $R^2$.

For compounds which are processed from solution, suitable substituents are, in particular, also long alkyl groups, for example having 5 to 10 C atoms, where these alkyl groups are preferably branched, or, in particular, also substituted or unsubstituted oligoarylene groups. Suitable oligoarylene groups are, for example, terphenyl, in particular meta-terphenyl and branched terphenyl, or quaterphenyl, in particular meta-quaterphenyl and branched quaterphenyl.

The above-mentioned embodiments, in particular the preferred embodiments, can be combined with one another as desired.

Examples of compounds in accordance with the above-mentioned embodiments, as can preferably be employed in organic electronic devices, are the compounds of the following structures (1) to (38).

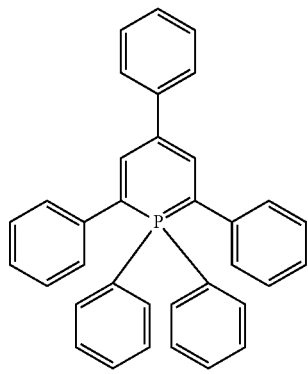

1

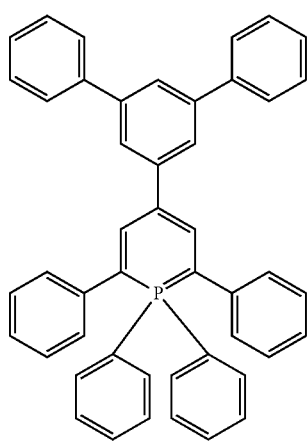

2

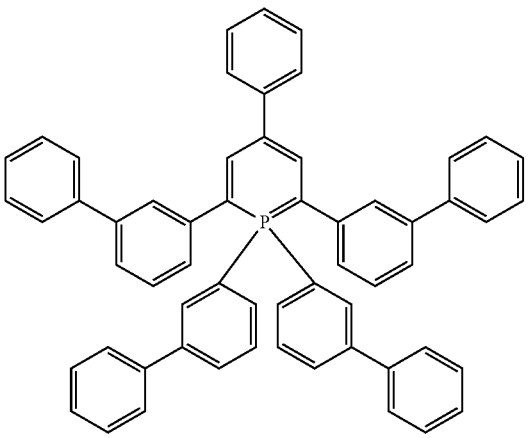

3

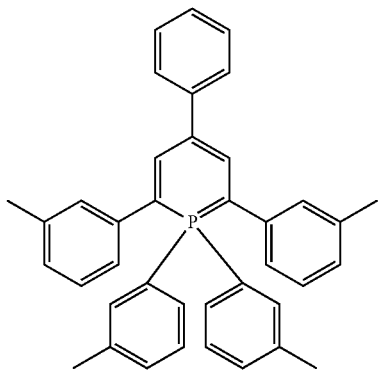

4

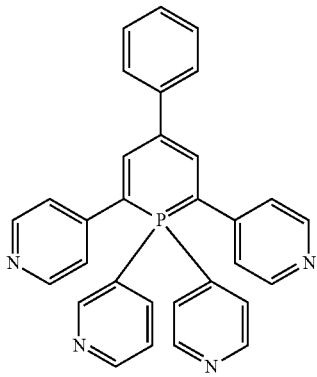

5

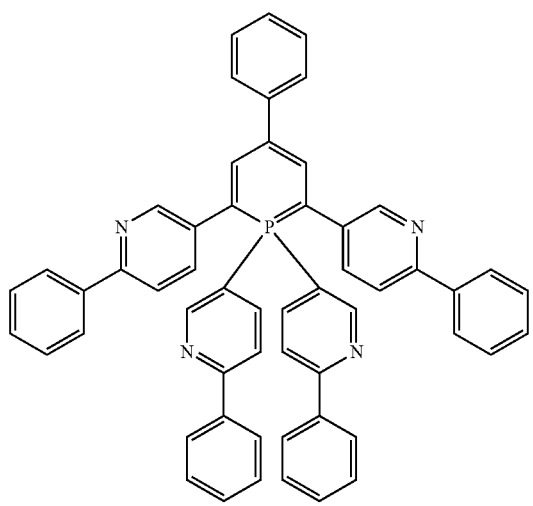
6
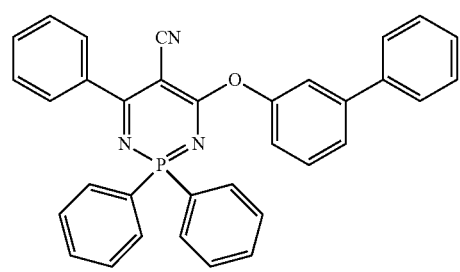
7
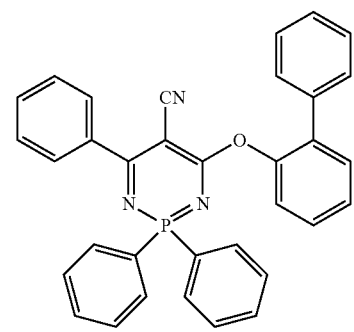
8
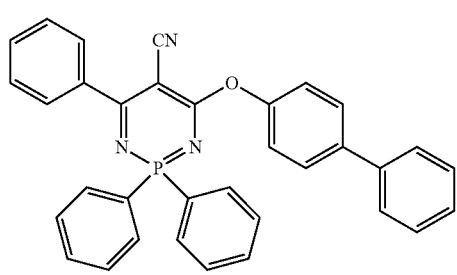
9
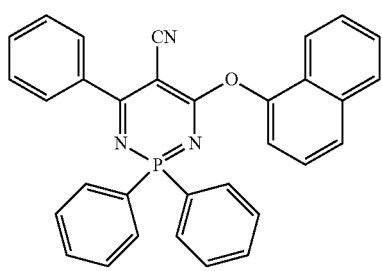
10
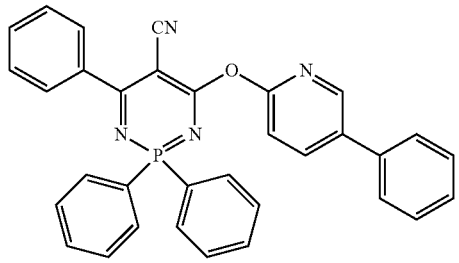
11
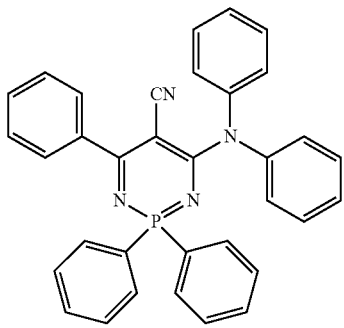
12
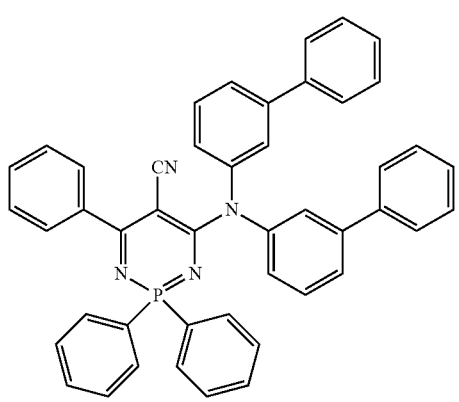
13
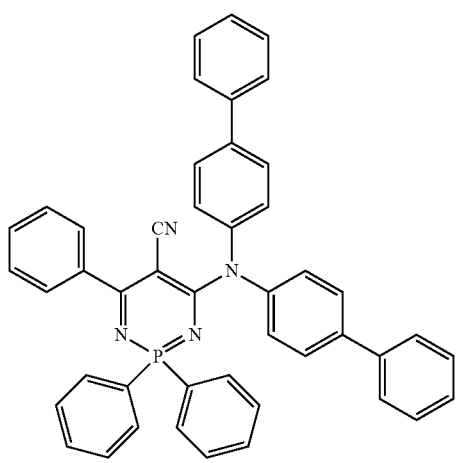
14

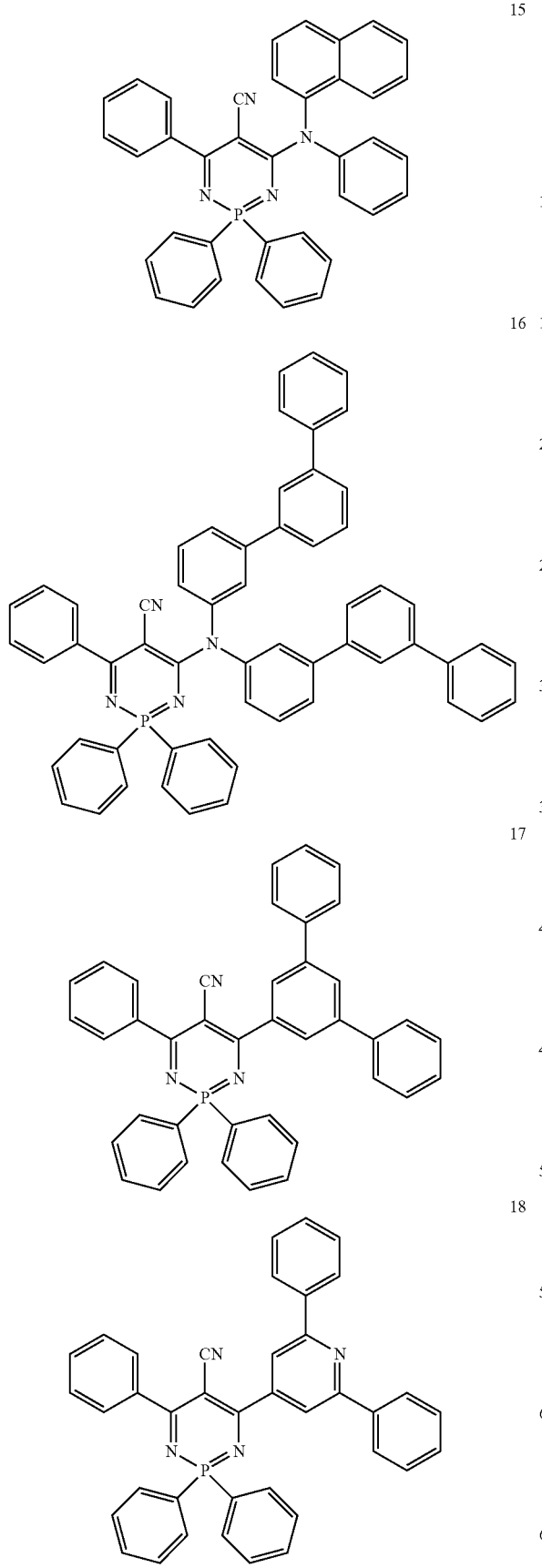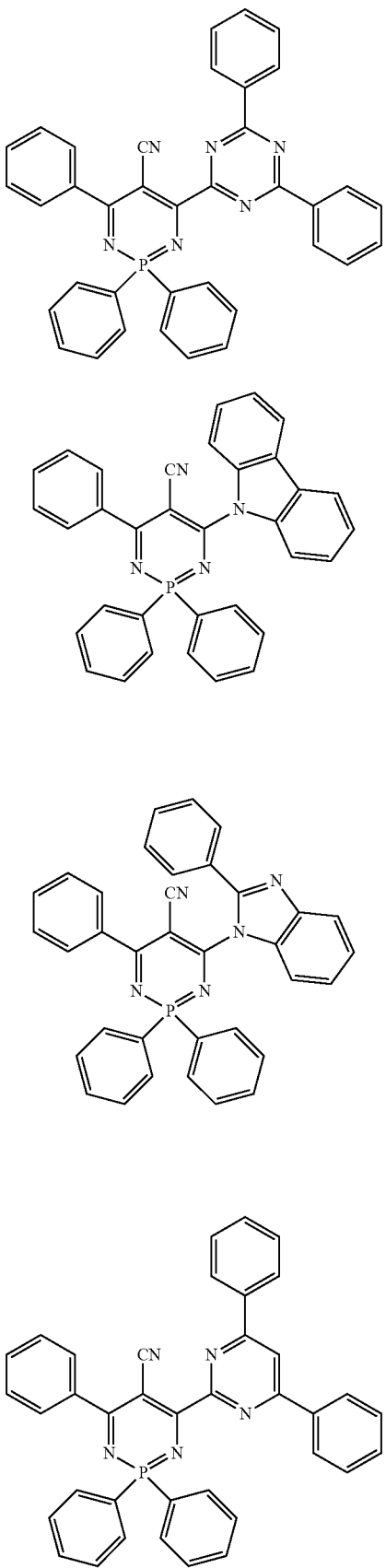

23
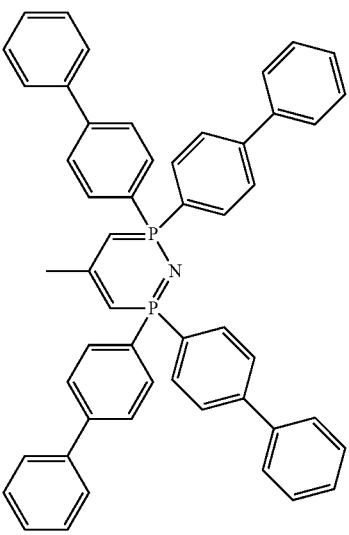 [SMILES: CC1=CP(c2ccc(-c3ccccc3)cc2)(c2ccc(-c3ccccc3)cc2)=NP(c2ccc(-c3ccccc3)cc2)(c2ccc(-c3ccccc3)cc2)=C1]
24
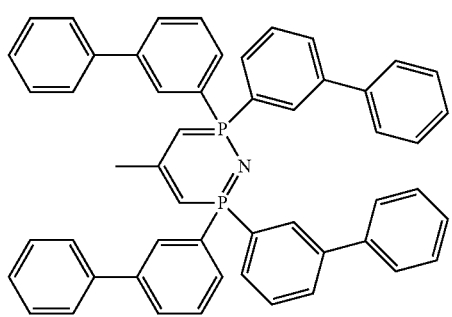 [SMILES: CC1=CP(c2cccc(-c3ccccc3)c2)(c2cccc(-c3ccccc3)c2)=NP(c2cccc(-c3ccccc3)c2)(c2cccc(-c3ccccc3)c2)=C1]
25
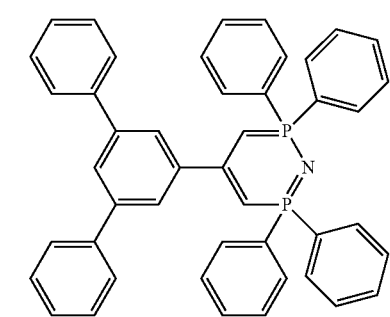
26
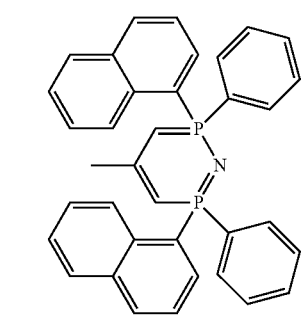
27
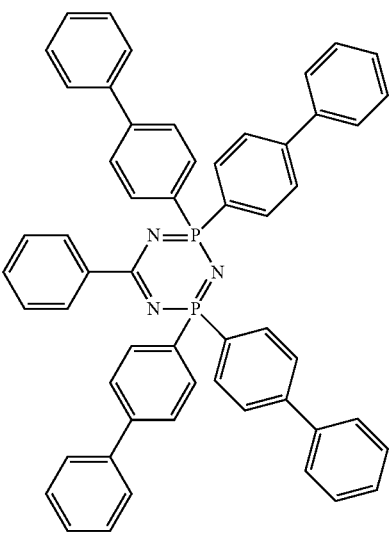 [SMILES: c1ccc(C2=NP(c3ccc(-c4ccccc4)cc3)(c3ccc(-c4ccccc4)cc3)=NP(c3ccc(-c4ccccc4)cc3)(c3ccc(-c4ccccc4)cc3)=N2)cc1]
28
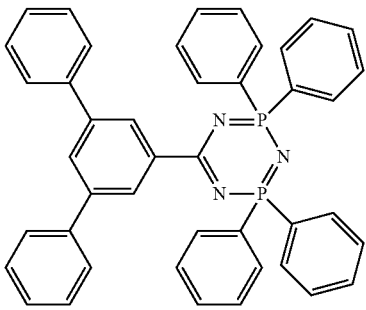
29
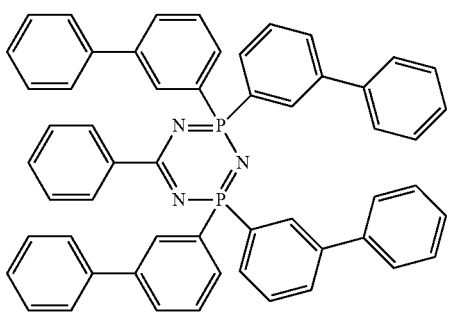

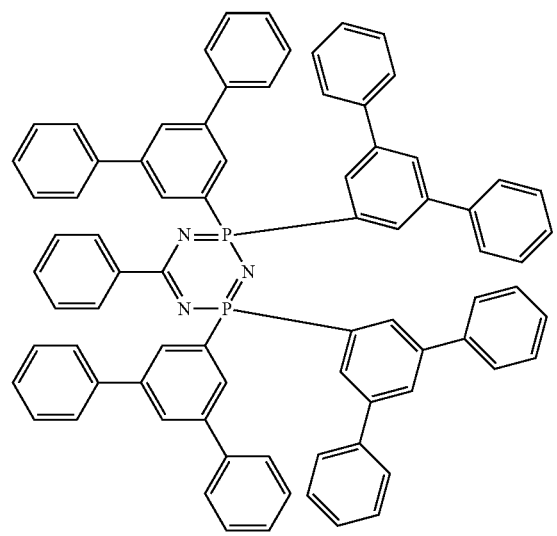
30
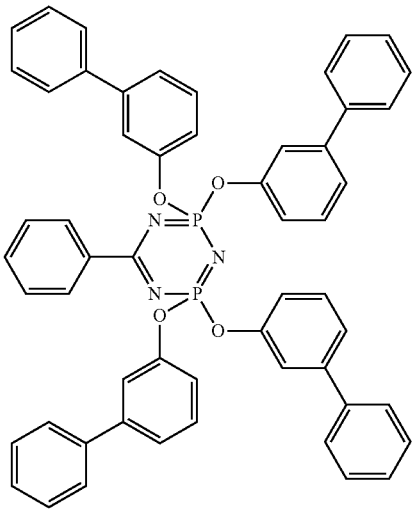
33
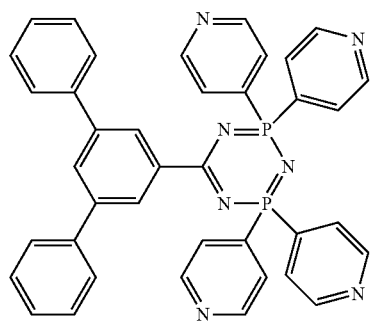
31
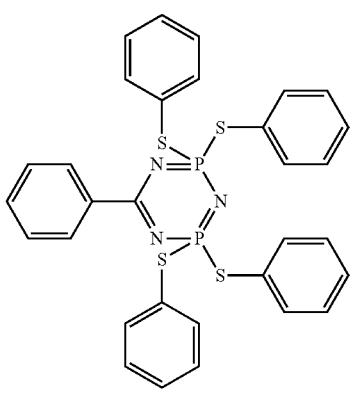
34
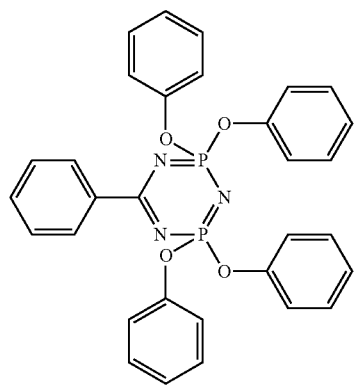
32
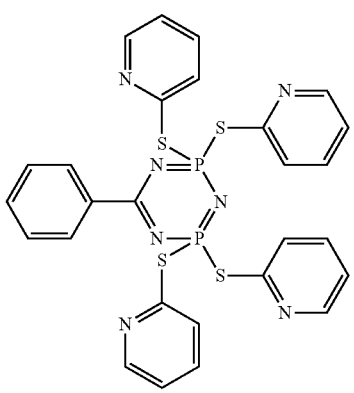
35

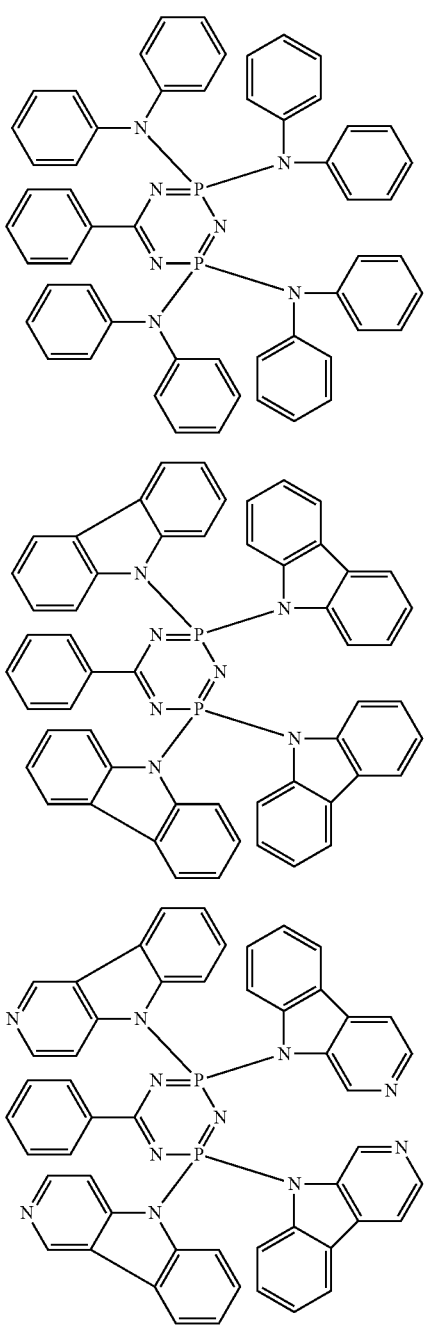

As mentioned above, the compounds of the formula (1) are used in an electronic device. An electronic device here is taken to mean a device which comprises at least one layer which comprises at least one organic compound. However, the component here may also comprise inorganic materials or also layers built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers), "organic plasmon emitting devices" (D. M. Koller et al., Nature Photonics 2008, 1-4) and electrophotography devices, preferably organic electroluminescent devices (OLEDs), particularly preferably phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013). Furthermore, an optical coupling-out layer may be applied to one or both of the electrodes.

The compound in accordance with the above-mentioned embodiments can be employed in various layers, depending on the precise structure. Preference is given to an organic electroluminescent device comprising one of the compounds of the formula (1), (2) or (3) to (6), (3a) to (6a) and (3b) to (6b) as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer and/or in an optical coupling-out layer. The above-mentioned preferred embodiments also apply to the use of the materials in organic electronic devices.

In a preferred embodiment of the invention, the compound of the formula (1), (2) or (3) to (6), (3a) to (6a) and (3b) to (6b) is employed as matrix material for a fluorescent or phosphorescent compound in an emitting layer. The organic electroluminescent device here may comprise one emitting layer or a plurality of emitting layers, where at least one emitting layer comprises at least one compound according to the invention as matrix material.

If the compound of the formula (1), (2) or (3) to (6), (3a) to (6a) and (3b) to (6b) is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state >1, in particular from an excited triplet state. For the purposes of this application, all luminescent complexes containing metals from the second and third transition-metal series, in particular all iridium and platinum complexes, and all luminescent copper complexes are to be regarded as phosphorescent compounds.

The mixture comprising the compound of the formula (1), (2) or (3) to (6), (3a) to (6a) and (3b) to (6b) and the emitting compound comprises between 99 and 1% by vol., preferably between 98 and 10% by vol., particularly preferably between 97 and 60% by vol., in particular between 95 and 80% by vol., of the compound of the formula (1), (2) or (3) to (6), (3a) to (6a) and (3b) to (6b), based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1), (2) or (3) to (6), (3a) to (6a) and (3b) to (6b) as matrix material for a phosphorescent emitter in combination with a further matrix material. Particularly suitable matrix materials which can be employed in combination with the compounds of the formula (1), (2) or (3) to (6), (3a) to (6a) and (3b) to (6b) are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or indenocarbazole derivatives, for example in accordance with WO 2010/136109 or the unpublished application DE 102009031021.5.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1), (2) or (3) to (6), (3a) to (6a) and (3b) to (6b) is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, Liq (lithium hydroxyquinolinate), or with alkali-metal salts, such as, for example, LiF.

In still a further preferred embodiment of the invention, the compound of the formula (1), (2) or (3) to (6), (3a) to (6a) and (3b) to (6b) is employed in a hole-blocking layer. A hole-blocking layer is taken to mean a layer which is directly adjacent to an emitting layer on the cathode side.

In still a further embodiment of the invention, the compound of the formula (1), (2) or (3) to (6), (3a) to (6a) and (3b) to (6b) is employed in a hole-transport layer or in an electron-blocking layer or exciton-blocking layer.

It is furthermore possible to use the compound of the formula (1), (2) or (3) to (6), (3a) to (6a) and (3b) to (6b) both in a hole-blocking layer or electron-transport layer and also as matrix in an emitting layer or both in a hole-transport layer or exciton-blocking layer and also as matrix in an emitting layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1), (2) or (3) to (6), (3a) to (6a) and (3b) to (6b) according to the invention.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. These processes are also particularly suitable for oligomers, dendrimers and polymers.

Likewise possible are hybrid processes, in which, for example, one or more layers are applied from solution and one or more other layers are applied by vacuum vapour deposition.

These processes are generally known to the person skilled in the art and can be applied by him without inventive step to organic electroluminescent devices comprising the compounds according to the invention.

The organic electroluminescent device according to the invention can be used, for example, in displays or for lighting purposes, but also for medical or cosmetic applications.

The compounds of the formula (1) and (2) mentioned above as preferred are novel and are thus likewise a subject-matter of the present invention.

The invention therefore relates to compounds of the formula (1') or (2'),

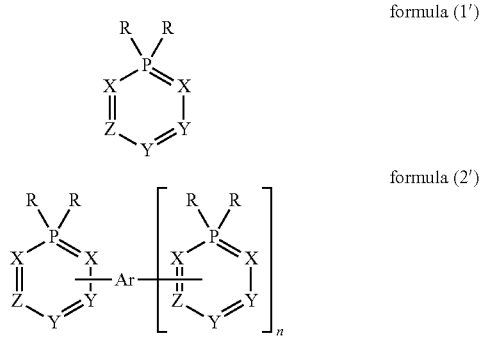

formula (1')

formula (2')

which have a molecular weight of greater than or equal to 500 g/mol and where the following applies to the symbols and indices used:

X, Y is on each occurrence, identically or differently, $CR^1$, N, P or $PR_2$, with the proviso that at least one group X or Y in compounds of the formula (1') stands for N;

Z is on each occurrence, identically or differently, $CR^1$ or N;

Ar is on each occurrence, identically or differently, an aromatic or heteroaromatic ring system having 5 to 60 aromatic ring atoms, which may be substituted by one or more radicals $R^1$;

R is on each occurrence, identically or differently, $CR^2=CR^2Ar^1$, a straight-chain alkyl group having 1 to 40 C atoms or a branched or cyclic alkyl group having 3 to 40 C atoms, each of which may be substituted by one or more radicals $R^2$, where one or more non-adjacent $CH_2$ groups which are not bonded directly to the phosphorus may also be replaced by $R^2C=CR^2$, $C≡C$, $Si(R^2)_2$, $Ge(R^2)_2$, $Sn(R^2)_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals $R^2$, or an aralkyl or heteroaralkyl group having 5 to 40 aromatic ring atoms, which may be substituted by one or more radicals $R^2$, or a combination of these systems; two or more substituents R together with the atoms to which they are bonded may also form a mono- or polycyclic aliphatic or aromatic ring system with one another here;

$R^1$ is on each occurrence, identically or differently, H, D, F, Cl, Br, I, $N(R^2)_2 N(Ar^1)_2$, C(=O)R$^2$, C(=O)Ar$^1$, P(=O)(Ar$^1$)$_2$, S(=O)Ar$^1$, S(=O)$_2$Ar$^1$, $CR^2=CR^2Ar^1$, CN, NO$_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems;

$Ar^1$ is on each occurrence, identically or differently, an aromatic or heteroaromatic ring system having 5 to 30 aromatic ring atoms, which may be substituted by one or more radicals $R^2$;

$R^2$ is selected from the group consisting of H, D, F, CN, aliphatic hydrocarbon radical having 1 to 20 C atoms, aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another;

n is 1 to 10, preferably 1, 2, 3, 4, 5 or 6;

the following compounds are excluded from the invention:

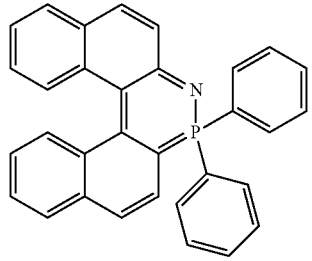

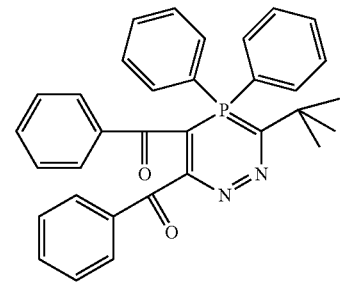

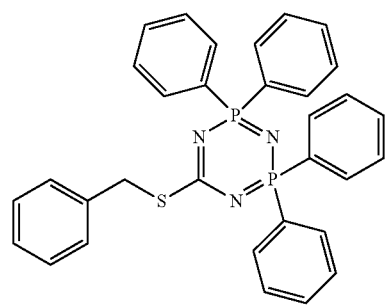

-continued

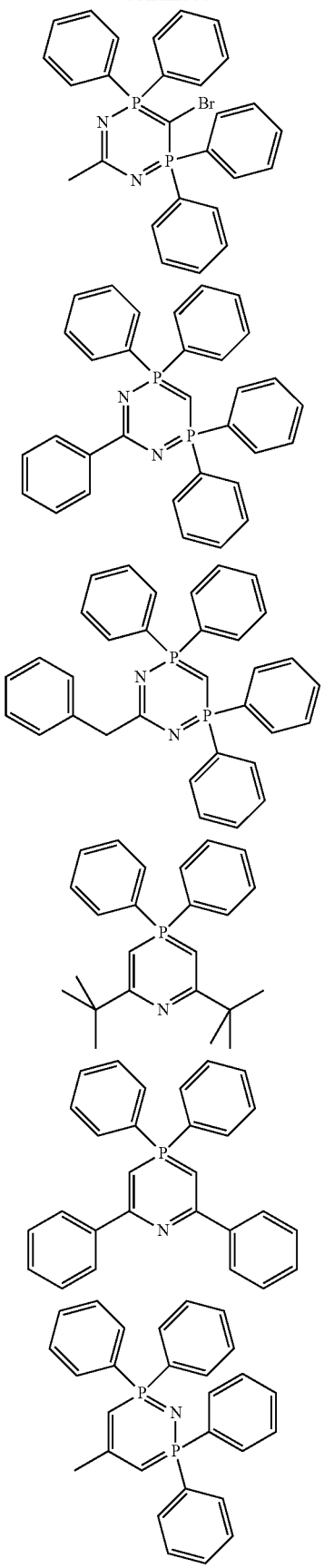

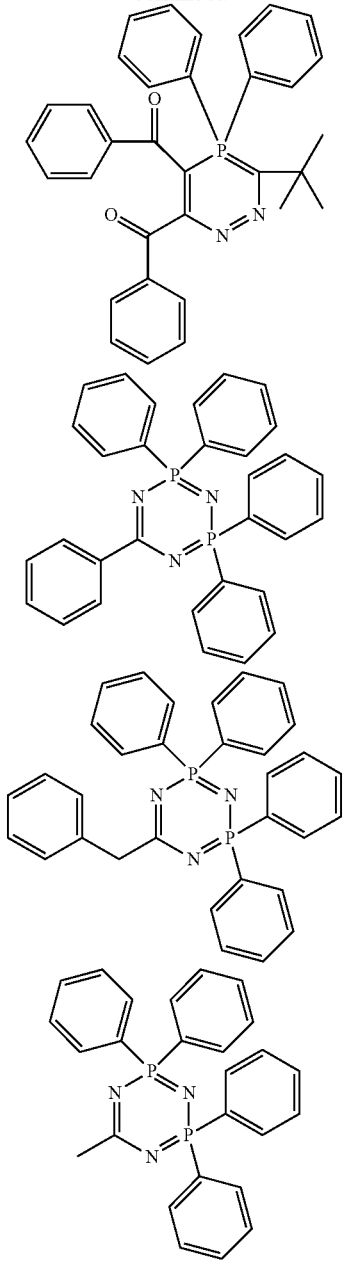

In a preferred embodiment of the invention, the molecular weight of the compounds of the formula (1') or (2') is greater than or equal to 700 g/mol.

For the compounds of the formula (1') or (2') according to the invention, the same preferences apply as already mentioned above for the electronic device. Thus, preferred structures are the structures of the above-mentioned formulae (3) to (6), (3a) to (6a) and (3b) to (6b) in which the other symbols and indices are selected correspondingly to the compounds of the formula (1') or (2').

The invention furthermore relates to the use of the compounds according to the invention in an electronic device.

The methods described below are suitable for the preparation of the compounds of the formula (1), (2), (1') and (2') or the preferred compounds according to the invention (the square brackets indicate the CAS numbers):

1) λ5-Phosphorines:

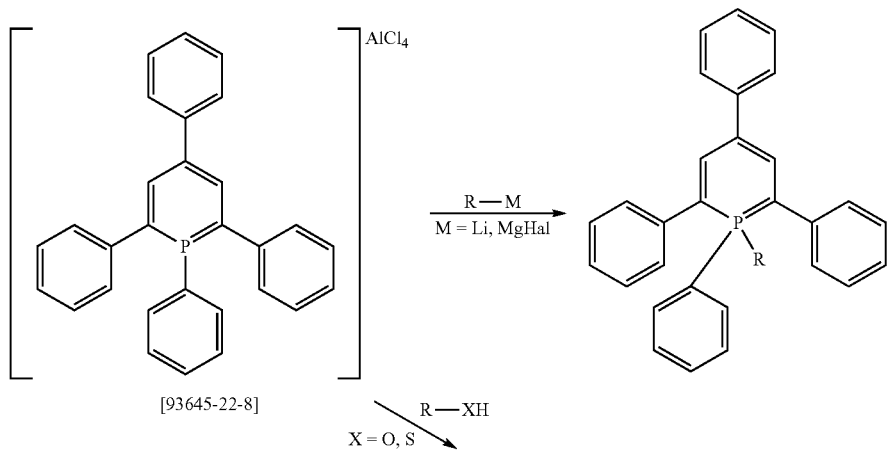

R = alkyl, aryl, heteroaryl

Phosphinium salts, such as 1,2,4,6-tetraphenylphosphinium tetrachloroaluminate, which is known from the literature, react with nucleophiles which contain, for example, C, N, O or S as nucleophilic atom, with formation of the derived λ5-phosphorines (T. N. Dave et al., *Angew. Chem.* 1984, 96(12), 984).

2) 1,3-Dizaa-2-phosphorines:

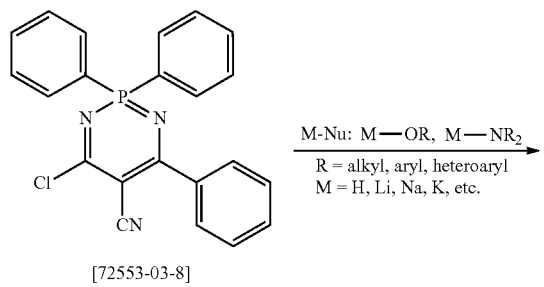

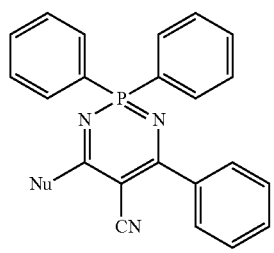

-continued

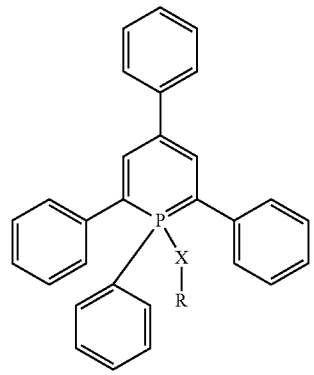

The 4-chloro-substituted 1,3-diaza-2-phosphorine shown above, which is known from the literature, can be functionalised using N- or O-nucleophiles to give a multiplicity of amino- or alkoxy-1,3-diaza-2-phosphorine derivatives (P. P. Kornuta et al., *Zhumal Obshchei Khimii* 1979, 49(10), 2201).

3) 1,3,5-Triaza-2-phosphorines:

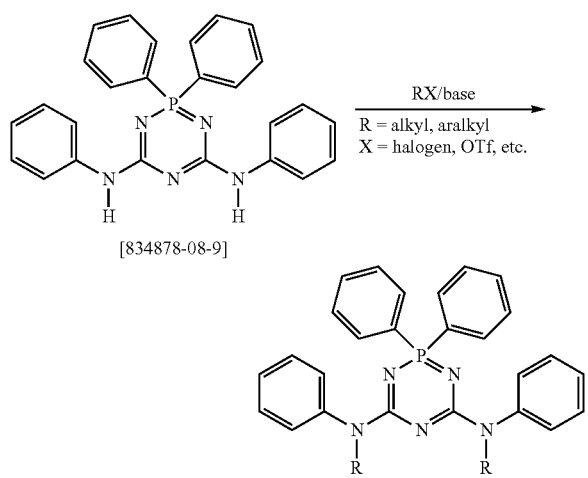

1,3,5,-Triaza-2-phosphorine-4,6-diamines can be obtained in accordance with N. Inguimbert et al., *Eur. J. Org. Chem.* 2004, 23, 4870 and reacted further, for example, with alkylating agents.

4) 2-Aza-1,3-diphosphorines:

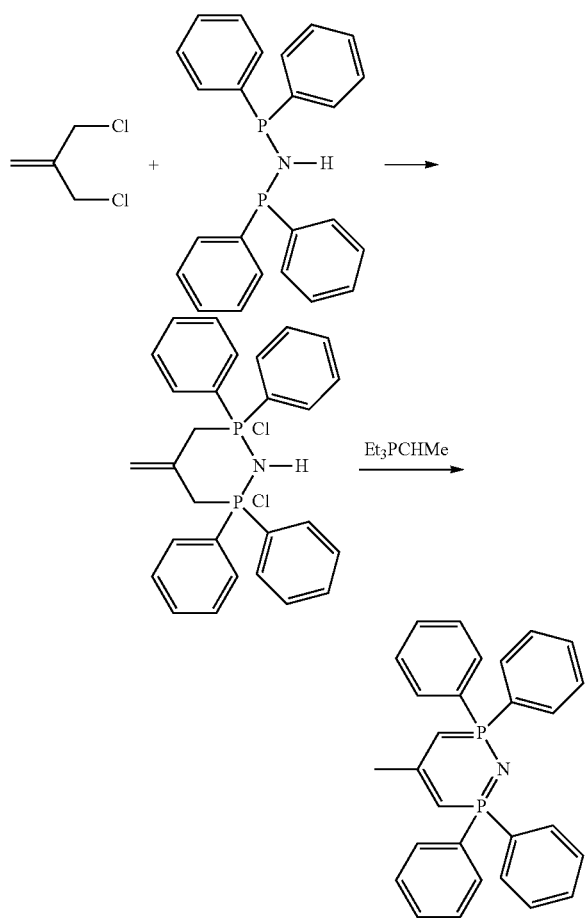

2-Aza-1,3-diphosphorines can be obtained in accordance with Schmidbaur et al., *Chem. Ber.* 1991, 124(7), 1525 from 1,1-bischloromethylethenes and bisdiphenylphosphinoamine. A suitable choice of the olefin or amine enables alkyl, aryl or heteroaryl derivatives of the above-mentioned basic structure to be obtained correspondingly.

5) 1,3,5-Triaza-2,4-diphosphorines:

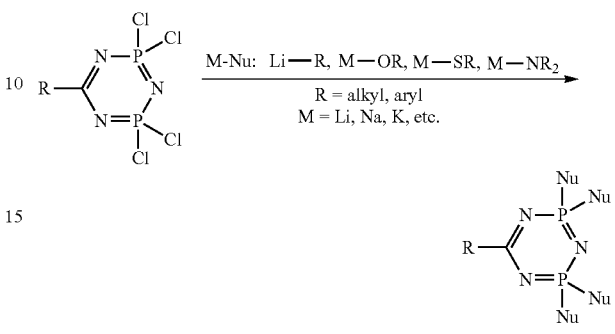

The 2,2,4,4-tetrachloro-2,4-diphosphatriazines described by Schmidpeter et al., *Inorg. Synth.* 1989, 25, 24-30 can be reacted with a multiplicity of C-, O-, S- or N-nucleophiles to give the correspondingly substituted 1,3,5-triaza-2,4-diphosphorines.

The present invention furthermore relates to a process for the preparation of the compounds according to the invention by preparation of the optionally substituted basic structure of the corresponding phosphacycle and introduction of further substituents in a subsequent step.

The compounds according to the invention and the electronic devices according to the invention, in particular organic electroluminescent devices, are distinguished by the following surprising advantages over the prior art:

1. The compounds according to the invention or compounds of the formula (1) and (2) or (3) to (6), (3a) to (6a) and (3b) to (6b) employed as matrix material for fluorescent or phosphorescent emitters result in high efficiencies and long lifetimes. This applies, in particular, if the compounds are employed as matrix material for a phosphorescent emitter.

2. The compounds according to the invention or compounds of the formula (1) and (2) or (3) to (6), (3a) to (6a) and (3b) to (6b) are not only suitable as matrix for green- and red-phosphorescent compounds, but instead in some cases also for blue-phosphorescent compounds.

3. The compounds according to the invention or compounds of the formula (1) and (2) or (3) to (6), (3a) to (6a) and (3b) to (6b) also exhibit good properties on use as electron-transport material.

4. The compounds according to the invention have high thermal stability and exhibit virtually no pyrolytic decomposition on sublimation.

5. The compounds according to the invention, employed in organic electroluminescent devices, result in high efficiencies and in steep current/voltage curves with low use voltages.

The invention is explained in greater detail by the following examples, without wishing to restrict it thereby. The person skilled in the art will be able to carry out the invention throughout the range disclosed from the descriptions and prepare further complexes according to the invention without inventive step and use them in electronic devices or use the process according to the invention.

EXAMPLES

The following syntheses are, unless indicated otherwise, carried out under a protective-gas atmosphere in dried solvents. The solvents and reagents can be purchased from ALDRICH or ABCR. The numbers indicated in square brackets represent the CAS numbers.

Example 1

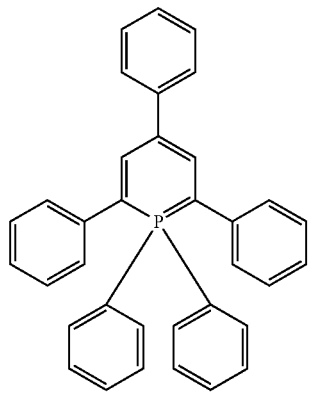

1,1-Dihydro-1,1,2,4,6-pentaphenylphosphorine can be prepared in accordance with T. N. Dave et al., *Angew. Chem.* 1984, 96(12), 984 from 1,2,4,6-tetraphenylphosphinium tetrachloroaluminate and phenyllithium and purified by multiple fractional sublimation ($p=5\times10^{-6}$ mbar, $T=195°$ C.).

Example 2

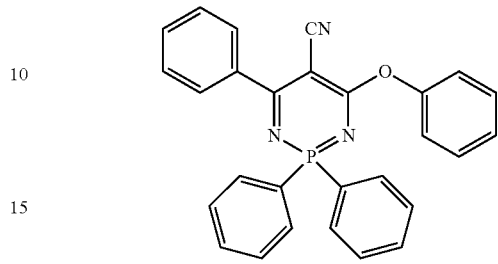

5-Cyano-2,2-dihydro-4-phenoxy-2,2,6-triphenyl-1,3-diaza-2-phosphorine can be prepared in accordance with P. P. Kornuta et al., *Zhurnal Obshchei Khimii* 1979, 49(10), 2201 and purified by multiple fractional sublimation ($p=5\times10^{-6}$ mbar, $T=220°$ C.).

The following compounds are obtained analogously by reaction of 4-chloro-5-cyano-2,2-dihydro-2,2,6-triphenyl-1,3-diaza-2-phosphorine with the alcoholates of the alcohols shown:

| Ex. | Alcohol | Product | Yield |
|-----|---------|---------|-------|
| 3 | 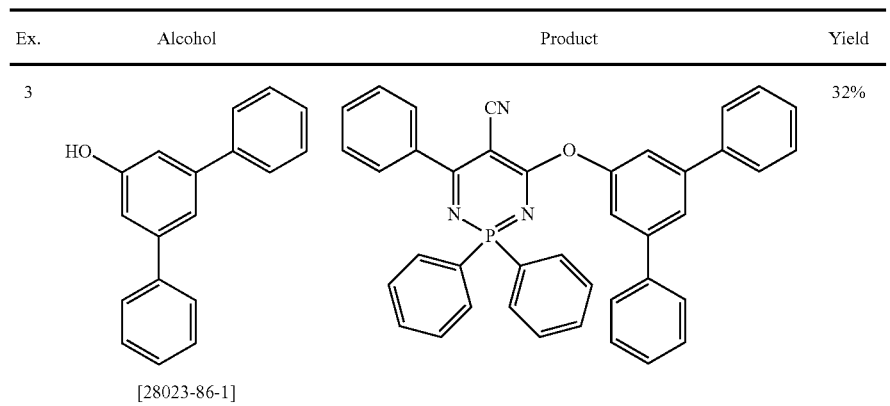 [28023-86-1] | | 32% |
| 4 | 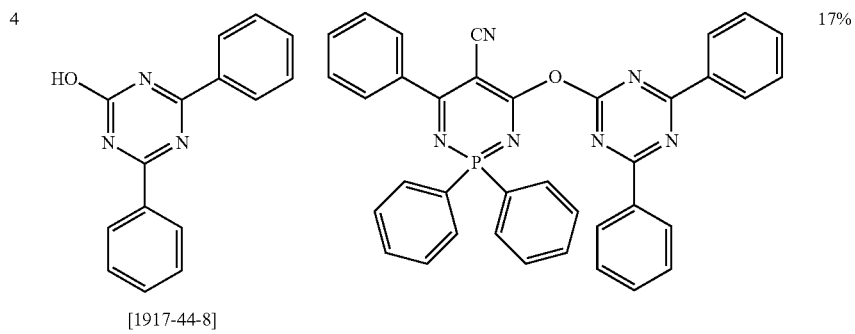 [1917-44-8] | | 17% |

Example 5

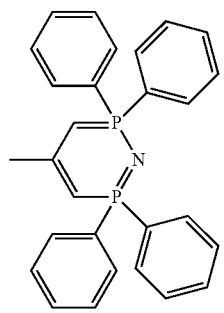

2,2,6,6-Tetrahydro-4-methyl-2,2,6,6-tetraphenyl-2-aza-1,6-diphosphorine can be prepared in accordance with Schmidbaur et al., *Chem. Ber.* 1991, 124(7), 1525, from 1,1-bischloromethylethene and bis(diphenylphosphino)amine and purified by multiple fractional sublimation (p=5×10⁻⁶ mbar, T=230° C.).

The following compounds are obtained analogously by reaction of the bis(diarylphosphino)amines (prepared from the diarylphosphines and ammonia in accordance with K. Blann et al., *J. Catal.* 2007, 249(2), 244):

Example 8

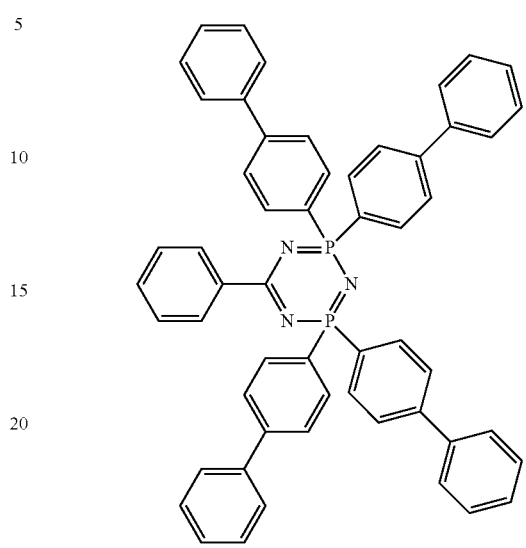

| Ex. | Bis(diarylphosphino)amine | Product | Yield |
|---|---|---|---|
| 6 | | | 48% |
| 7 | | | 40% |

40 ml (100 mmol) of n-BuLi (2.5 M in hexane) are added dropwise to a solution, cooled to −78° C., of 23.3 g (100 mmol) of 4-bromobiphenyl in 500 ml of THF, and the mixture is subsequently stirred for a further 15 min. A solution of 6.7 g, (20 mmol) of 2,2,4,4-tetrachloro-2,2,4,4-tetra-hydro-6-phenyl-1,3,5-triaza-2,4-diphosphorine [21893-50-5] in 200 ml of THF is subsequently added dropwise to the solution, and the mixture is subsequently stirred at −78° C. for a further 3 h. After slow warming to room temperature, the THF is removed in vacuo, the residue is taken up in 200 ml of dichloromethane and filtered through a short column with aluminium oxide (neutral, activity grade 1). After removal of the solvent, the residue is purified by multiple fractional sublimation (p=5×10$^{-6}$ mbar, T=300° C.). Yield: 5.2 g, (6.5 mmol), 32%.

The following compounds are obtained analogously by reaction of the corresponding aryllithium compounds:

| Ex. | Aryllithium compounds | Product | Yield |
|---|---|---|---|
| 9 | [86632-30-6] | | 45% |
| 10 | [16669-47-9] | | 22% |

Example 11

Production and Characterisation of Organic Electroluminescent Devices

Electroluminescent devices according to the invention can be produced as described in general, for example, in WO 2005/003253. The results for various OLEDs are compared here. The basic structure, the materials used, the degree of doping and the layer thicknesses thereof are identical for better comparability.

OLEDs comprising compounds 1, 3, 4, 7 and 10 according to the invention as host material in the following layer structure are described:

Hole-injection layer (HIL) 20 nm of 2,2',7,7'-tetrakis(di-para-tolyl-amino)spiro-9,9'-bifluorene Hole-transport layer (HTL) 5 nm of NPB (N-naphthyl-N-phenyl-4,4'-diaminobiphenyl)
Electron-blocking layer (EBL) 15 nm of EBL (9,9-bis-(3,5-diphenylaminophenyl)fluorene)
Emission layer (EML): 40 nm
Host: see Table 1
Dopant: 10% by vol. doping, fac-tris(2-phenylpyridine)iridium (IrPPy) or tris(1-phenylisoquinoline)iridium (IrPIQ)
Electron conductor (ETL) 20 nm of BAlq
Cathode 1 nm of LiF, 100 nm of Al on top.
The structures of EBL and the dopants are depicted below for clarity.

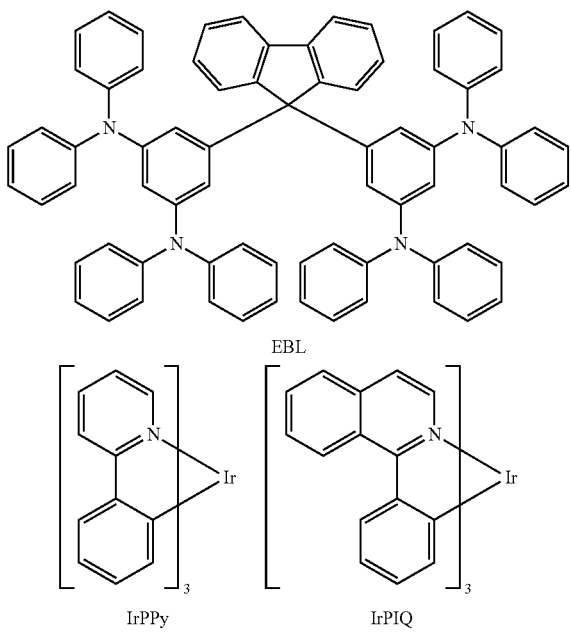

EBL

IrPPy    IrPIQ

In order to characterise these OLEDs, the electroluminescence spectra, the external quantum efficiency (measured in %) as a function of the luminance, calculated from current/voltage/luminance characteristic lines (IUL characteristic lines), are determined.

TABLE 1

Device results

| Example | Host/dopant | EQE at 100 cd/m² [%] | Voltage at 100 cd/m² [V] | CIE x/y |
|---|---|---|---|---|
| 12 | Example 1 IrPIQ | 6.6 | 3.8 | 0.69/0.31 |
| 13 | Example 3 IrPIQ | 8.3 | 4.6 | 0.69/0.31 |
| 14 | Example 4 IrPIQ | 11.1 | 4.3 | 0.69/0.31 |
| 15 | Example 7 IrPIQ | 12.7 | 4.8 | 0.68/0.31 |
| 16 | Example 10 IrPPy | 14.6 | 5.0 | 0.36/0.60 |

Furthermore, OLEDs comprising the compounds from Example 4, 8 and 9 as electron conductor in the following layer structure are produced:
Hole-injection layer (HIL) 20 nm of 2,2',7,7'-tetrakis(di-para-tolyl-amino)spiro-9,9'-bifluorene
Hole-transport layer (HTL) 5 nm of NPB (N-naphthyl-N-phenyl-4,4'-diaminobiphenyl)

Emission layer (EML) 40 nm
Host: 4,4'-N,N'-dicarbazolylbiphenyl (CBP)
Dopant: 10% by vol. doping, tris(1-phenylisoquinoline)iridium (IrPIQ)
Electron conductor (ETL) 20 nm, see Table 2
Cathode 1 nm of LiF, 100 nm of Al on top.

In order to characterise these OLEDs, the electroluminescence spectra, the external quantum efficiency (measured in %) as a function of the luminance, calculated from current/voltage/luminance characteristic lines (IUL characteristic lines), are determined.

TABLE 2

Device results

| Device Example | ETL | EQE at 100 cd/m² [%] | Voltage at 100 cd/m² [V] | CIE x/y |
|---|---|---|---|---|
| 17 | Example 4 | 13.1 | 4.2 | 0.69/0.31 |
| 18 | Example 8 | 11.0 | 4.0 | 0.69/0.31 |
| 19 | Example 9 | 12.7 | 3.8 | 0.68/0.31 |

The invention claimed is:

1. An organoelectroluminescent device comprising at least one compound of formula (1'),

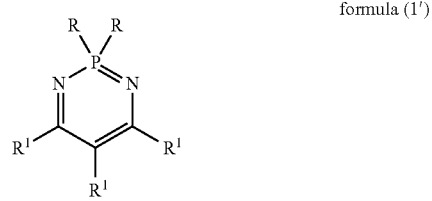

formula (1')

wherein:
R is, identically or differently on each occurrence an aromatic or heteroaromatic ring system having 5 to 24 aromatic ring atoms optionally substituted by one or more radicals $R^2$, or two or more substituents R together with the phosphorous atom to which they are bonded optionally define a mono- or polycyclic aliphatic or aromatic ring system with one another;
$R^1$ is, identically or differently on each occurrence, H, $N(Ar^1)_2$, CN, a straight-chain alkyl or alkoxy, group having 1 to 40 C atoms, or a branched or cyclic alkyl or alkoxy, group having 3 to 40 C atoms, each of which is optionally substituted by one or more radicals $R^2$, or an aromatic or heteroaromatic ring system having 5 to 60 aromatic ring atoms optionally substituted by one or more radicals $R^2$, an aryloxy or heteroaryloxy group having 5 to 40 aromatic ring atoms optionally substituted by one or more radicals $R^2$;
$R^2$ is selected from the group consisting of H, CN, aliphatic hydrocarbon radicals having 1 to 20 C atoms, and aromatic or heteroaromatic ring systems having 5 to 30 aromatic ring atoms, and wherein two or more adjacent substituents $R^2$ optionally form a mono- or polycyclic, aliphatic, aromatic, or heteroaromatic ring system with one another.

2. The device of claim 1, wherein the radicals R are, identically or differently on each occurrence, selected from the group consisting of an aromatic or heteroaromatic ring system having 5 to 24 aromatic ring atoms, optionally substituted by one or more radicals $R^2$.

3. The device of claim 1, wherein the radicals R are bonded to the same phosphorus atom, defining a spiro ring system.

4. The device of claim 1, wherein the radical $R^1$ is, identically or differently on each occurrence, selected from the group consisting of H, $N(Ar^1)_2$, $C(=O)Ar^1$, CN, a straight-chain alkyl or alkoxy group having 1 to 10 C atoms or a branched or cyclic alkyl or alkoxy group having 3 to 10 C atoms, optionally substituted by one or more radicals $R^2$, or an aromatic or heteroaromatic ring system having 5 to 30 aromatic ring atoms optionally substituted by one or more radicals $R^2$.

5. The organic electroluminescent device of claim 1, wherein said compound of formula (1') is employed as matrix material for fluorescent or phosphorescent emitters.

6. The organic electroluminescent device of claim 1, wherein said compound of formula (1') is employed in a hole-blocking layer, and/or in an electron-transport layer, and/or in an electron-blocking or exciton-blocking layer, and/or in a hole-transport layer, and/or in an optical coupling-out layer, and/or as matrix material for phosphorescent emitters.

* * * * *